(12) United States Patent
Zheng

(10) Patent No.: US 11,410,348 B2
(45) Date of Patent: Aug. 9, 2022

(54) IMAGING METHOD AND DEVICE

(71) Applicant: Telefield Medical Imaging Limited, Hong Kong (HK)

(72) Inventor: Yongping Zheng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 958 days.

(21) Appl. No.: 16/096,697

(22) PCT Filed: Apr. 26, 2016

(86) PCT No.: PCT/CN2016/080261
§ 371 (c)(1),
(2) Date: Oct. 26, 2018

(87) PCT Pub. No.: WO2017/185240
PCT Pub. Date: Nov. 2, 2017

(65) Prior Publication Data
US 2020/0126270 A1 Apr. 23, 2020

(51) Int. Cl.
G06T 11/00 (2006.01)
A61B 8/08 (2006.01)
A61B 8/00 (2006.01)
G06T 7/00 (2017.01)

(52) U.S. Cl.
CPC ............ *G06T 11/005* (2013.01); *A61B 8/085* (2013.01); *A61B 8/0875* (2013.01); *A61B 8/4245* (2013.01); *A61B 8/466* (2013.01); *A61B 8/483* (2013.01); *G06T 7/0016* (2013.01); *G06T 2207/10132* (2013.01); *G06T 2207/30008* (2013.01); *G06T 2207/30012* (2013.01); *G06T 2207/30056* (2013.01); *G06T 2207/30068* (2013.01); *G06T 2207/30096* (2013.01); *G06T 2211/428* (2013.01)

(58) Field of Classification Search
None
See application file for complete search history.

(56) References Cited

U.S. PATENT DOCUMENTS

2012/0004545 A1* 1/2012 Ziv-Ari ............... A61B 8/0883
600/437

FOREIGN PATENT DOCUMENTS

CN 102125443 A 7/2011

OTHER PUBLICATIONS

International Search Report of PCT Patent Application No. PCT/CN2016/080261 dated Jan. 26, 2017.

* cited by examiner

*Primary Examiner* — Leon Flores

(57) ABSTRACT

An imaging method. The method comprises the following steps: determining a target by identifying target-related position information or characteristic information (S101); implementing a two-dimensional scan of the target to collect image data of the target in a three-dimensional space (S102); processing, during the scanning, and on a real-time basis, the image data and relevant spatial information to obtain a plurality of image contents of the target, and displaying the image content on a real-time basis (S103); and arranging the plurality of image contents in an incremental sequence to form an image of the target (S104). The imaging method prevents collection of unusable image information, shortens image data collection time, and increases the speed of an imaging process. The application further provides an imaging device.

18 Claims, 3 Drawing Sheets

IMAGING METHOD AND DEVICE

FIELD OF THE APPLICATION

The present application relates to the field of image processing, and more particularly, relates to an imaging method and device.

BACKGROUND OF THE APPLICATION

In the X-ray imaging mode, an X-ray beam is used to illuminate an area, and an image in the entire area is formed by projection. Similarly, magnetic resonance imaging (MRI) and computed tomography (CT) reconstruct the image of the entire area by collecting the data needed in a certain area.

In some imaging modalities, such as ultrasound imaging, optical coherence tomography, and terahertz imaging, imaging generally has one-dimensional to three-dimensional stages, such as single location with depth information, two-dimensional (2D) images, and three-dimensional (3D) images. A number of scan types, such as manual, mechanical or electronic scans, can be used to acquire a large number of low-dimensional images for constructing multi-dimensional images, for example, from 2D to 3D. In general, this is a relatively time consuming process, especially when the scan range is large (as opposed to a single frame imaging window). Therefore, these imaging methods are actually incremental. However, the incremental image features are invisible for most of the imaging time because the device shows the complete image after the sub-dimension image acquisition. At the same time, it takes a long time to use a probe for conducting 2D imaging to form a wide range of 3D ultrasound images.

At present, there are some methods for incremental imaging, but the purpose of these methods is to provide a fast or real-time display of reconstructed partial volume by incremental means, for example, during the entire scanning process, after each B-type or a large number of B-type images are acquired, the volume image is incrementally presented instead of performing image reconstruction after collecting all the required data. Because image reconstruction usually takes a relatively long time after collecting all the required data. Some methods can also provide a three-dimensional orthogonal view in terms of reconstructing and displaying incremental volumes. However, the principle of target-based incremental imaging is not addressed in the prior art, and for any imaging, the most important is the target of imaging, such as tumor and spinal structures in ultrasound images.

SUMMARY OF THE APPLICATION

The technical problem to be solved by the present application is to provide an imaging method and device for target-based incremental imaging in view of the deficiencies of the prior art.

The technical solution of the present application to solve the above problems is to provide an imaging method, wherein, the method comprises the following steps:

S1, determining a target by identifying target-related position information or characteristic information;

S2, implementing a two-dimensional scan of the target to collect image data of the target in a three-dimensional space;

S3, during the scanning, processing the image data and relevant spatial information on a real-time basis, to obtain a plurality of image contents of the target, and displaying the image content on a real-time basis;

S4, arranging a plurality of image contents on an incremental sequence, to form an image of the target.

In the imaging method of the present application, in the step S2, the method further includes when detecting that the position of the two-dimensional scan is not within a certain range of the target, automatically pausing and giving a visual or audible prompt and restarting after returning to the range of the target.

In the imaging method of the present application, the method further includes the following step:

when detecting that some part of the image of the target has not been imaged or the image quality of a part of the image of the target is poor, re-scanning the part to make the part having good image quality.

In the imaging method of the present application, in the step S2, further includes implementing a multi-angle two-dimensional scan of the target to obtain more image information about the target to enhance the image of the target.

In the imaging method of the present application, in the step S4, before arranging the plurality of image contents on an incremental sequence, further includes processing image smoothing and filtering between adjacent image contents.

In the imaging method of the present application, in the step S4, the order of incrementing is determined by the scanning order of the target.

In the imaging method of the present application, in the step S3, further includes displaying the image content within a preset time.

In the imaging method of the present application, in the step S1, further includes determining a plurality targets having different characteristic information.

In the imaging method of the present application, the imaging method further includes:

if there is a plurality of different targets, during the scanning, transforming scanning the plurality of different targets.

In the imaging method of the present application, in the step S1, the determination of the target is achieved by referring to the related image that has been obtained before.

In the imaging method of the present application, in the step S1, the determination of the target is achieved by performing a two-dimensional or three-dimensional pre-scan within a certain range.

In the imaging method of the present application, the two-dimensional scanning is realized by an ultrasonic probe equipped with a three-dimensional locator.

In the imaging method of the present application, the image of the target is a surface image or a projected image.

In the imaging method of the present application, when the target is selected, its approximate position and shape will be marked on the display device for reference in the two-dimensional scan described in S2.

The present application further provides an imaging device, wherein, includes:

a target determining device, configured for determining a target by identifying target-related position information or characteristic information;

a data collecting device, configured for implementing a two-dimensional scan of the target to collect image data of the target in a three-dimensional space;

an image content obtaining and displaying unit, configured for processing the image data and relevant spatial information on a real-time basis, to obtain a plurality of image contents of the target, and displaying the image content on a real-time basis during the scanning; and a target image forming device, configured for arranging a plurality of image contents on an incremental sequence, to form an image of the target.

In the imaging device of the present application, the data collecting device further includes a device configured for automatically pausing and giving a visual or audible prompt and restarting after returning to the range of the target when detecting that the position of the two-dimensional scan is not within a certain range of the target.

In the imaging device of the present application, further includes a device configured for when detecting that some part of the image of the target has not been imaged or the image quality of a part of the image of the target is poor, rescanning the part to make the part having good image quality.

In the imaging device of the present application, the data collecting device further includes a device configured for implementing a multi-angle two-dimensional scan of the target to obtain more image information about the target to enhance the image of the target.

In the imaging device of the present application, the target image forming device further includes a device configured for before arranging the plurality of image contents on an incremental sequence, further includes processing image smoothing and filtering between adjacent image contents.

In the imaging device of the present application, the target determining device includes a device configured for performing a two-dimensional or three-dimensional pre-scan within a certain range, and further includes an ultrasonic probe equipped with a three-dimensional locator.

The imaging method and device embodying the present application have the beneficial effects: preventing collection of unusable image information, shortening image data collection time, and increasing the speed of an imaging process. Meanwhile, in the present application, when scanning is performed, two-dimensional scanning is employed based on the target to form a three-dimensional image, which further reduces the time taken for imaging consumption. Further, in the scanning process of the present application, the image content of the target is displayed in real time to improve the quality of the image. When the quality of the image is poor, it is not necessary to wait until the scan and reconstruction are completed to rescan the entire target, further reducing the imaging time.

BRIEF DESCRIPTION OF THE DRAWINGS

in FIG. 2(a), the target 2 is a cuboid; in FIG. 2(b), the target 2 is a curved surface body; in FIG. 2(c), the target 2 is a plane; in FIG. 2(d), target 2 is a curved surface; in FIG. 2(e), target 2 is a cylinder;

DETAILED DESCRIPTION OF THE PREFERRED EMBODIMENT

The present application provides an imaging method. In the imaging method, a target is first determined; then based on the target, during the scanning, by processing the image data and relevant spatial information of the target on a real-time basis, the image content of the target is obtained, and the image content of the target is displayed on a real-time basis, the obtained image content of the target is arranged on an incremental sequence to form the image of the target. The imaging method prevents collection of unusable image information, shortens image data collection time, and increases the speed of an imaging process. Meanwhile, in the present application, when scanning is performed, two-dimensional scanning is employed based on the target to form a three-dimensional image, which further reduces the time taken for imaging consumption. Further, in the scanning process of the present application, the image content of the target is displayed in real time to improve the quality of the image. When the quality of the image is poor, it is not necessary to wait until the scan and reconstruction are completed to rescan the entire target, further reducing the imaging time. Here, the image of the target is a surface image or a projected image.

In order to make the objects, technical solutions and advantages of the present application more comprehensible, the present application will be further described in detail below with reference to the accompanying drawings and embodiments. It is understood that the specific embodiments described herein are merely illustrative of the application and are not intended to limit the application.

Figure 1:
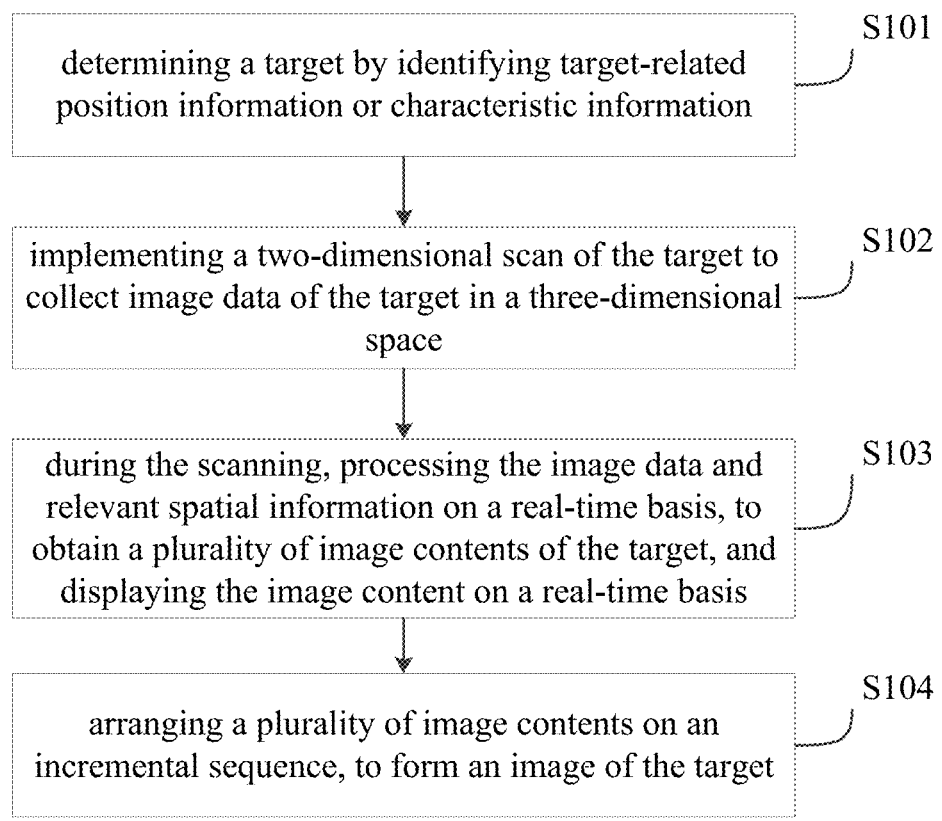
FIG. 1 is a flow chart of an imaging method according to an embodiment of the present application.
Figure 2A:
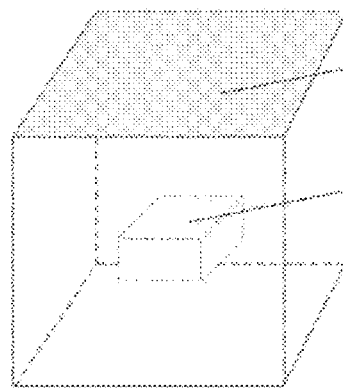
FIG. 2(a)-(e) are diagrams showing an example of a target in an imaging method according to an embodiment of the present application; wherein, 1 indicates the three-dimensional space in which the target is located.
Figure 2B:
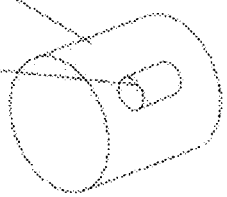
Figure 2C:
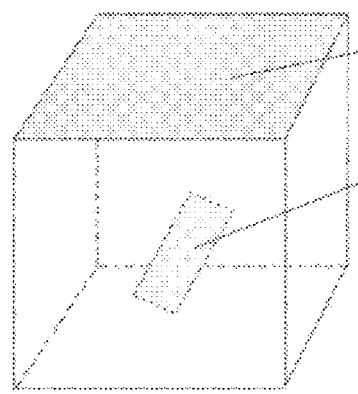
Figure 2D:
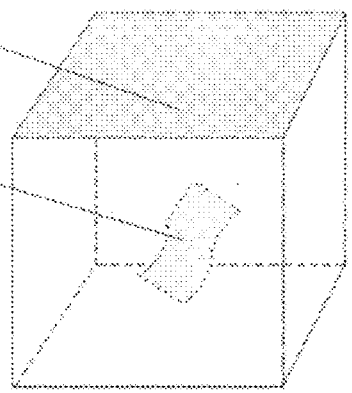
Figure 2E:
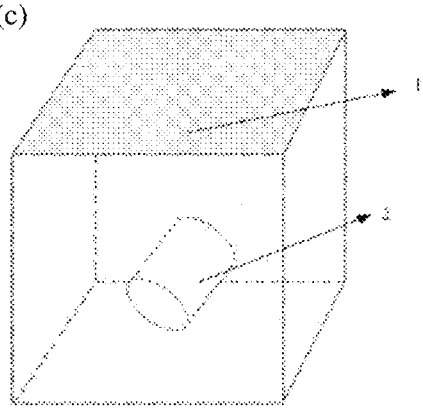

As shown in FIG. 1, which is a flow chart of an imaging method according to an embodiment of the present application, the method includes the following steps:

S101, determining a target by identifying target-related position information or characteristic information;

In this step, the position information or the characteristic information are all predefined, wherein the position information is recorded by a known spatial positioning technique. The target is located in the three-dimensional space, for example, a tumor in the breast, a liver in the human body, a bone in the limb, a spine in the body, a plane or a curved surface inside the body. As shown in FIG. 2(a)-(e), which are diagrams showing an example of a target in an imaging method according to an embodiment of the present application, 1 indicates the three-dimensional space in which the target is located, in FIG. 2(a), the target 2 is a cuboid; in FIG. 2(b), the target 2 is a curved surface body; in FIG. 2(c), the target 2 is a plane; in FIG. 2(d), target 2 is a curved surface; in FIG. 2(e), target 2 is a cylinder. The target is also located in a two-dimensional space, such as a diseased tissue in an X-ray image.

Here, the determination of the target is achieved by referring to the related image that has been obtained before.

S102, implementing a two-dimensional scan of the target to collect image data of the target in a three-dimensional space;

In this step, the scanning method can be manual scanning or mechanical scanning or mechanically assisted manual scanning That is the two-dimensional scanning is realized by an ultrasonic probe equipped with a three-dimensional locator.

In another embodiment, the warning function may also be set in the above steps. That is when detecting that the position of the two-dimensional scan is not within a certain range of the target, automatically pausing and giving a visual or audible prompt and restarting after returning to the range of the target.

In another embodiment, an image enhancement link can also be set in the above steps. That is implementing a multi-angle two-dimensional scan of the target to obtain more image information about the target to enhance the image of the target.

S103, during the scanning, processing the image data and relevant spatial information on a real-time basis, to obtain a plurality of image contents of the target, and displaying the image content on a real-time basis;

In this step, the image content is a partial image of the target, and the real-time processing includes processing immediately after acquiring each image data, without waiting for all the images to be collected for processing. Wherein the image data comprises one frame or several frame images. Processing methods include pixel brightness post processing, image smoothing, and noise removal. Wherein, the pixel brightness post-processing includes a grayscale enhanced threshold window processing. In order to increase the contrast of the image, a gray threshold window is selected for enhancement, and the grayscale outside the gray threshold window is compressed or omitted. This allows the target to be highlighted on the image, improving the recognition of the target, usually using a linear transformation to enhance the grayscale. The image smoothing adopts the averaging method, i.e. low-pass filtering; the noise removal can be performed by the averaging method, including time averaging, spatial compounding and frequency fusion, etc. This part of the content belongs to the prior art and will not be described here. In this embodiment, the real-time processing further includes performing image reconstruction on the image content in the same or adjacent space immediately after obtaining one or several frames of images to get the image content representing the location and display it in real time according to the corresponding spatial location. Wherein, image reconstruction includes average processing.

S104, arranging a plurality of image contents on an incremental sequence, to form an image of the target.

In this step, before arranging the plurality of image contents on an incremental sequence, further includes implementing related processing between adjacent image contents for better images, and the related processing includes image smoothing and filtering operations, as well as image fusion of edges of adjacent image content.

In this embodiment, the order of incrementing is determined by the scanning order of the target.

In this embodiment, in the scanning process, after the determined image content is processed in real time, the image content in the preset time may also be displayed, and the image content in the plurality of preset times is arranged in an incremental manner according to the scanning order to form an image of the target. The reference point of the preset time may be some rhythmic physiological signals of the human body, such as the electrocardiogram signal of the human body. Of course, before the image content of the plurality of preset times is arranged in an incremental manner, the related image content may also be subjected to related processing. For this part, it has been described above, and details are not described herein again.

In another embodiment of the imaging method of the present application, when the target is selected, its approximate position and shape will be marked on the display device for reference in the two-dimensional scan described in S102.

In another embodiment of the imaging method of the present application, the imaging method further includes:

when detecting that some part of the image of the target has not been imaged or the image quality of a part of the image of the target is poor, rescanning the part and then proceeding to step S103 to make the part having good image quality. This interactive step, monitoring, can be monitored manually or by computer. In such a case, there is no need to rescan the entire target when scanning and reconstruction is completed, thereby reducing the time required for imaging.

In this embodiment, the imaging method further includes identifying multiple targets with different characteristic information for incremental imaging during scanning.

In this embodiment, the imaging method further includes:

if there is a plurality of different targets, during the scanning, transforming scanning the plurality of different targets.

For the imaging method provided by the present application, the imaging method will be described in detail below for the application of the imaging method to the B-mode ultrasound image of the back of the human body from the bottom end to the top end.

First, the target is determined, wherein the target is a plane defined by a curved surface relating to the morphology of the spine at a certain depth under the skin of the back surface.

Figure 3:
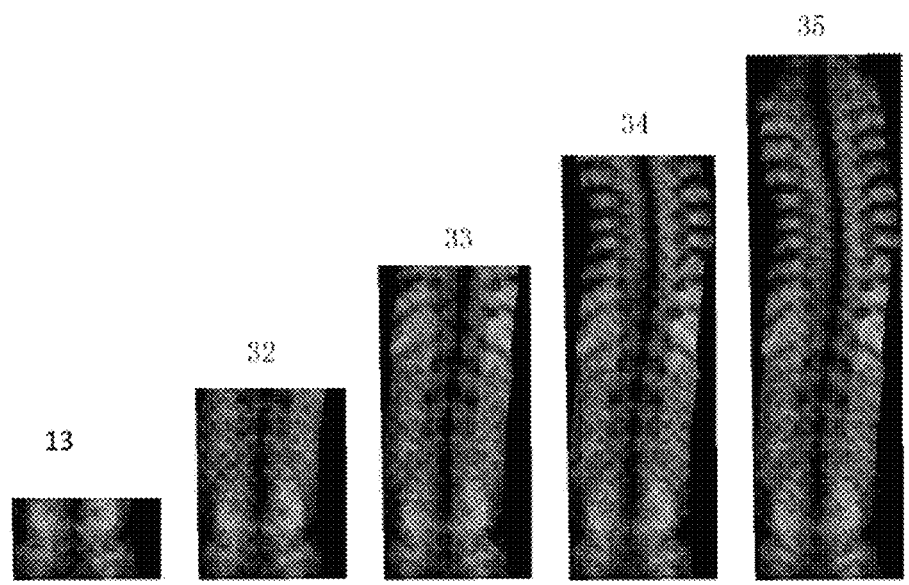
FIG. 3 is an incremental spine image obtained by applying the imaging method of the present application to ultrasound imaging.

Secondly, the ultrasound probe in the ultrasound imaging system is used to scan the back of the human body. The main part of the ultrasound imaging system adopts the above imaging method to obtain an incremental spine image as shown in FIG. 3. As can be seen from the figure, viewed from left to right, the image content of the real-time display during the scanning process, respectively, has a first image 31, a second image 32, a third image 33, a fourth image 34, and a fifth image 35. And the latter image includes the previous image, that is, the image content is arranged in an ascending manner to form a complete spine image (i.e., the fifth image 35).

The imaging method of the present application can also be applied to other imaging modes with scanning.

Figure 4:
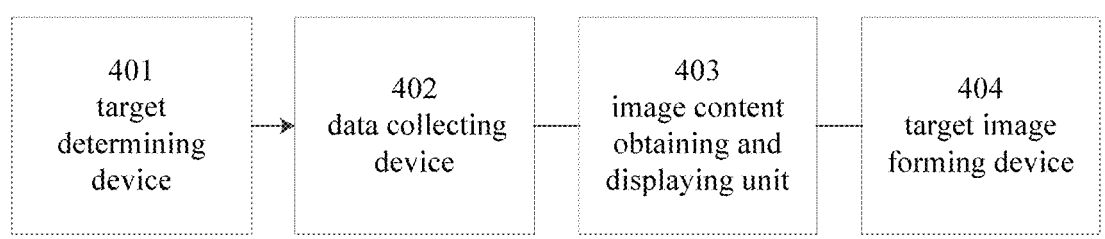
FIG. 4 is a schematic diagram of an embodiment of an imaging device of the present application.

In the embodiment of the imaging device of the present application shown in FIG. 4, the device includes a target determining device 401, configured for determining a target by identifying target-related position information or characteristic information; a data collecting device 402, configured for implementing a two-dimensional scan of the target to collect image data of the target in a three-dimensional space; an image content obtaining and displaying unit 403, configured for processing the image data and relevant spatial information on a real-time basis, to obtain a plurality of image contents of the target, and displaying the image content on a real-time basis during the scanning; and a target image forming device 404, configured for arranging a plurality of image contents on an incremental sequence, to form an image of the target.

The data collecting device 402 further includes a device configured for automatically pausing and giving a visual or audible prompt and restarting after returning to the range of the target when detecting that the position of the two-dimensional scan is not within a certain range of the target. The data collecting device 402 further includes a device configured for implementing a multi-angle two-dimensional scan of the target to obtain more image information about the target to enhance the image of the target.

The imaging device further includes a device configured for when detecting that some part of the image of the target has not been imaged or the image quality of a part of the image of the target is poor, rescanning the part to make the part having good image quality.

The target image forming device 404 further includes further includes a device configured for before arranging the plurality of image contents on an incremental sequence, further includes processing image smoothing and filtering between adjacent image contents. The target determining device 401 includes a device configured for performing a two-dimensional or three-dimensional pre-scan within a certain range, and further includes an ultrasonic probe equipped with a three-dimensional locator.

In summary, in the imaging method and device of the present application, a target is first determined; then based on the target, during the scanning, by processing the image data and relevant spatial information of the target on a real-time basis, the image content of the target is obtained, and the image content of the target is displayed on a real-time basis, the obtained image content of the target is arranged on an incremental sequence to form the image of the target. The imaging method prevents collection of unusable image information, shortens image data collection time, and increases the speed of an imaging process.

The above description is only a preferred embodiment of the present application. However, the scope of the present application is not limited thereto, and any changes or substitutions that can be easily conceived within the scope of the present application are within the scope of the present application. Therefore, the scope of protection of the present application should be determined by the scope of protection of the claims.

The invention claimed is:

1. An imaging method, wherein, the method comprises the following steps: S1, determining a target by identifying target-related position information or characteristic information; S2, implementing a two-dimensional scan of the target to collect image data of the target in a three-dimensional space; S3, during the scanning, processing the image data and relevant spatial information on a real-time basis, to obtain a plurality of image contents of the target, and displaying the image content on a real-time basis; S4, arranging a plurality of image contents on an incremental sequence, to form an image of the target; in the step S2, the method further includes when detecting that the position of the two-dimensional scan is not within a certain range of the target, automatically pausing and giving a visual or audible prompt and restarting after returning to the range of the target.

2. The imaging method according to claim 1, wherein, the method further includes the following step: when detecting that some part of the image of the target has not been imaged or the image quality of a part of the image of the target is poor, rescanning the part to make the part having good image quality.

3. The imaging method according to claim 1, wherein, in the step S2, further includes implementing a multi-angle two-dimensional scan of the target to obtain more image information about the target to enhance the image of the target.

4. The imaging method according to claim 1, wherein, in the step S4, before arranging the plurality of image contents on an incremental sequence, further includes processing image smoothing and filtering between adjacent image contents.

5. The imaging method according to claim 1, wherein, in the step S4, the order of incrementing is determined by the scanning order of the target.

6. The imaging method according to claim 5, wherein, the imaging method further includes: when there are a plurality of different targets, during the scanning, the target to be scanned can be changed among the plurality of different targets.

7. The imaging method according to claim 1, wherein, in the step S3, further includes displaying the image content within a preset time.

8. The imaging method according to claim 1, wherein, in the step S1, further includes determining a plurality targets having different characteristic information.

9. The imaging method according to claim 1, wherein, in the step S1, the determination of the target is achieved by referring to the related image that has been obtained before.

10. The imaging method according to claim 1, wherein, in the step S1, the determination of the target is achieved by performing a two-dimensional or three-dimensional pre-scan within a certain range.

11. The imaging method according to claim 1, wherein, the two-dimensional scanning is realized by an ultrasonic probe equipped with a three-dimensional locator.

12. The imaging method according to claim 1, wherein, the image of the target is a surface image or a projected image.

13. The imaging method according to claim 1, wherein, when the target is selected, its approximate position and shape will be marked on the display device for reference in the two-dimensional scan described in S2.

14. A imaging device, wherein, includes: a target determining device, configured for determining a target by identifying target-related position information or characteristic information; a data collecting device, configured for implementing a two-dimensional scan of the target to collect image data of the target in a three-dimensional space; an image content obtaining and displaying unit, configured for processing the image data and relevant spatial information on a real-time basis, to obtain a plurality of image contents of the target, and displaying the image content on a real-time basis during the scanning; and a target image forming device, configured for arranging a plurality of image contents on an incremental sequence, to form an image of the target; the data collecting device further includes a device configured for automatically pausing and giving a visual or audible prompt and restarting after returning to the range of the target when detecting that the position of the two-dimensional scan is not within a certain range of the target.

15. The imaging device according to claim 14, wherein, further includes a device configured for when detecting that some part of the image of the target has not been imaged or the image quality of a part of the image of the target is poor, rescanning the part to make the part having good image quality.

16. The imaging device according to claim 14, wherein, the data collecting device further includes a device configured for implementing a multi-angle two-dimensional scan of the target to obtain more image information about the target to enhance the image of the target.

17. The imaging device according to claim 14, wherein, the target image forming device further includes a device configured for before arranging the plurality of image contents on an incremental sequence, further includes processing image smoothing and filtering between adjacent image contents.

18. The imaging device according to claim 14, wherein, the target determining device includes a device configured for performing a two-dimensional or three-dimensional pre-scan within a certain range, and further includes an ultrasonic probe equipped with a three-dimensional locator.

* * * * *